(12) United States Patent
Bhandari et al.

(10) Patent No.: US 11,654,256 B2
(45) Date of Patent: May 23, 2023

(54) VENTILATOR SYSTEM AND METHOD THEREOF

(71) Applicants: Sudarshan Kumar Bhandari, Indore (IN); Purnima Bhandari, Indore (IN)

(72) Inventors: Sudarshan Kumar Bhandari, Indore (IN); Purnima Bhandari, Indore (IN)

(73) Assignees: Sudarshan Kumar Bhandari, Indore (IN); Purnima Bhandari, Indore (IN)

( * ) Notice: Subject to any disclaimer, the term of this patent is extended or adjusted under 35 U.S.C. 154(b) by 410 days.

(21) Appl. No.: 16/896,467

(22) Filed: Jun. 9, 2020

(65) Prior Publication Data

US 2021/0316103 A1 Oct. 14, 2021

(51) Int. Cl.
*A61M 16/00* (2006.01)
*A61M 16/08* (2006.01)
(Continued)

(52) U.S. Cl.
CPC .... *A61M 16/0858* (2014.02); *A61M 16/0003* (2014.02); *A61M 16/024* (2017.08); *A61M 16/0833* (2014.02); *A61M 16/1005* (2014.02); *A61M 16/109* (2014.02); *A61M 16/209* (2014.02); *A61M 2016/0027* (2013.01); *A61M 2202/0208* (2013.01); *A61M 2205/16* (2013.01); *A61M 2205/3337* (2013.01); *A61M 2205/3348* (2013.01); *A61M 2205/502* (2013.01)

(58) Field of Classification Search
CPC ............ A61M 16/0858; A61M 16/101; A61M 16/0003; A61M 16/0833; A61M 16/1005; A61M 16/109; A61M 2205/16; A61M 2205/3348; G01F 1/37
See application file for complete search history.

(56) References Cited

U.S. PATENT DOCUMENTS 4,537,079 A * 8/1985 Lee ........................... G01L 7/18
  73/747
5,895,862 A * 4/1999 Peabody ................. G01L 7/187
  73/747

(Continued)

FOREIGN PATENT DOCUMENTS

CA    2782371 A1 *  6/2011   ........ A61M 16/0057
DE  202005014511 U1 *  1/2006   ............. G01L 13/00
(Continued)

*Primary Examiner* — Philip R Wiest
*Assistant Examiner* — Sarah B Lederer
(74) *Attorney, Agent, or Firm* — Shumaker, Loop & Kendrick, LLP

(57) ABSTRACT

A ventilator system including an oxygen delivery cylinder, an air delivery unit, connecting tubes, and a digital display unit. The system further includes a Y connector configured to mix air and oxygen, to form a gas and pass said gas towards an outlet of the system. A water manometer that is configured to monitor a pressure of the gas in the system and blow off the excess pressure of the gas. A solenoid valve that is configured to adjust an end respiratory pressure obtained from a breathing device connected to the outlet of the system. The pressure of the gas being instantly delivered to the breathing device is measured by water manometer from a dead space near the outlet, thereby enabling a dual monitoring of the gas pressure being delivered to the breathing device.

11 Claims, 2 Drawing Sheets

(51) Int. Cl.
*A61M 16/10* (2006.01)
*A61M 16/20* (2006.01)

(56) References Cited

U.S. PATENT DOCUMENTS

| | | | |
|---|---|---|---|
| 6,450,164 B1 * | 9/2002 | Banner | A61M 16/042 |
| | | | 128/207.15 |
| 7,347,205 B2 | 3/2008 | Levi | |
| 10,420,906 B2 | 9/2019 | Colburn | |
| 2002/0014237 A1 * | 2/2002 | Richey, II | B01D 53/04 |
| | | | 128/203.25 |
| 2004/0231673 A1 | 11/2004 | Reissmann | |
| 2005/0124866 A1 * | 6/2005 | Elaz | A61M 16/0051 |
| | | | 128/920 |
| 2009/0241953 A1 * | 10/2009 | Vandine | A61M 16/12 |
| | | | 128/204.21 |
| 2018/0126105 A1 | 5/2018 | Pesenti et al. | |

FOREIGN PATENT DOCUMENTS

| | | | | |
|---|---|---|---|---|
| EP | 0482261 A1 * | 10/1990 | | |
| EP | 0482261 A1 * | 4/1992 | | |
| EP | 0768095 A2 | 4/1997 | | |
| WO | WO-9731670 A1 * | 9/1997 | | A61M 16/085 |
| WO | 2018033863 A1 | 2/2018 | | |

* cited by examiner

VENTILATOR SYSTEM AND METHOD THEREOF

CROSS-REFERENCE TO RELATED APPLICATIONS AND PRIORITY

The present application does claim priority from Indian Patent Application No. 202021016052 filed on 14 Apr. 2020.

TECHNICAL FIELD

The present subject matter described herein, in general, relates to a field of biomedical devices. In particular, the present subject matter is related to a ventilator system and a method thereof.

BACKGROUND

A ventilator is a device to deliver the required oxygenation to a patient's lungs with stipulated pressure and full safety. Existing ventilator systems are configured to provide oxygen in the system through wall oxygen system which is highly pressured. It is important to deliver respiratory pressure to a limit that won't harm the patient's lungs, while keeping end respiratory pressure (PBEP) not allowing lungs to fully deflate. Preterm infants sometimes face respiratory distress and require respiratory support. Intermittent positive airway pressure (IPAP) Continuous Positive Airway Pressure (CPAP) is one or the method to provide the required respiratory support. While providing said respiratory support to the patient, it is important that the pressure in the ventilation system is maintained and no excess pressure may be delivered to the patient. Moreover, such respiratory support may be required in any emergency situations. The existing ventilator systems comprise a spring-based dial monitor and a plurality of valves that are susceptible to get stuck.

The existing ventilators also use a plurality of electronic pressure sensors in order to detect and monitor the pressure of gas in the ventilator, wherein the gas is a mixture of air and oxygen. This makes the electronic circuitry in the ventilator systems complex and expensive. In case if the pressure sensors get damaged or fail while monitoring the patient, it is difficult to find out exact error in the electronic circuitry. Moreover, it is important to also keep a check on the pressure of the gas nearby the mouth of the patient in order to ensure the exact amount of gas being delivered to the patient. Such a check without using a different pressure sensor in the system is currently not present in the existing systems.

Therefore, the existing ventilator systems comprise high pressure wall oxygen delivery system, plurality of valves that may get choked, a spring-based dial monitor, a plurality of electronic pressure sensors, expensive tubing, and such like. The existing systems are completely closed leading to difficulty in finding the error in components which may damage while monitoring or providing ventilation. The existing ventilator systems are thus complex, expensive, difficult to port, require skilled person, continuous power supply, high pressure oxygen supply, excess assembly time, excess maintenance and excess components to build the system.

Thus, there is a long-standing need for an improved ventilator system and a method of operating the same that alleviates the aforementioned technical challenges/drawbacks.

SUMMARY

This summary is provided to introduce concepts related to a ventilator system and a method thereof. This summary is not intended to identify essential features of the claimed subject matter nor is it intended for use in determining or limiting the scope of the claimed subject matter.

In one aspect a ventilator system is illustrated in accordance with the present subject matter. The ventilator system may comprise an oxygen delivery cylinder, an air delivery unit and a plurality of connecting tubes. The ventilator system may further comprise a Y connector configured to mix air and oxygen, to form a gas and pass said gas towards an outlet of the ventilator system. The air and oxygen are received from the air delivery unit and the oxygen delivery unit respectively. The system further may comprise a water manometer configured to monitor a pressure of the gas in the ventilator system and blow off the excess pressure of the gas through a channel. The system may comprise a solenoid valve configured to adjust an end respiratory pressure, wherein the end respiratory pressure is obtained from a breathing device. The breathing device is connected to the outlet of the ventilator system. The system may comprise a digital display unit to display a plurality of measurements associated with the gas in the ventilator system. The pressure of the gas being instantly delivered to the breathing device by the ventilation system is measured by said water manometer from a dead space. The dead space is near the outlet of the ventilator system, thereby enabling a dual monitoring of the pressure of the gas being delivered to the breathing device.

In another aspect, a method for the ventilator system is illustrated in accordance with the present subject matter. The method may comprise delivering oxygen via an oxygen delivery cylinder to the ventilator system. The method may comprise delivering air via air delivery unit to the ventilator system. The method may comprise mixing the air and oxygen in a Y connector, to form a gas, and passing said gas towards an outlet of the ventilator system wherein, the air and oxygen is received from the air delivery unit and the oxygen delivery unit respectively. The method may comprise monitoring a pressure of the gas in the ventilator system via a water manometer and blowing off the excess pressure of the gas through a channel. The pressure of the gas being instantly delivered to the breathing device by the ventilation system is measured by said water manometer from a dead space, wherein the dead space is near the outlet of the ventilator system, thereby enabling a dual monitoring of the pressure of the gas being delivered to the breathing device. The method may comprise adjusting an end respiratory pressure via a solenoid valve. The end respiratory pressure is obtained from a breathing device. The breathing device is connected to the outlet of the ventilator system. The method may comprise displaying via a digital display unit a plurality of measurements associated with the gas in the ventilator system.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Embodiments described herein provide a ventilator system 100 and a method 200 of its use. The embodiments described herein are useful for patients of all ages including adults, children and newborn babies. Further, the embodiments can be used during transport of patients of all ages.

The ventilator system 100 may be used in the following modes:

1. The fundamental device with manual IPPV and CPAP.
2. The end respiratory pressure is generated with variable aperture size on respiratory circuit. This helps to give CPAP too.
3. A piston unit comprising solenoid valve and flow control knob is operated on simple computing code to obtain number of breaths per minute (variable 10 to 90/minute) which can be controlled and monitored.
4. A variable respiratory/expiratory ratio as per blood gas results of the patient may also be displayed.
5. CPAP (Continuous Positive Airway Pressure) on endotracheal tube/laryngeal mask and nasal prong may also be given by the ventilator system 100.

The ventilator system may receive oxygen from a cylinder and works with 12 volts power supply which makes this unit Ambulatory.

If there is a power failure, the stated ventilator system 100 may still provide the breath manually, by blocking the aperture or using Ambu Bag. Further, even if the oxygen finishes, the patient's lungs can still receive the air through ventilator system 100 with pressure already generated.

All the open tubing in the ventilator system 100 are directly visible and easily explainable. Even, the paramedics' staff can use this system. The mechanics and usage of this system can easily be explained to any medical staff via phone, as nothing is concealed. This ventilator system 100 is electric & pressure driven unlike the existing systems which are volume/gas device. The cost of the ventilator system 100 would be the fraction of currently existing ventilator systems used in the mainstream market.

Figure 1:
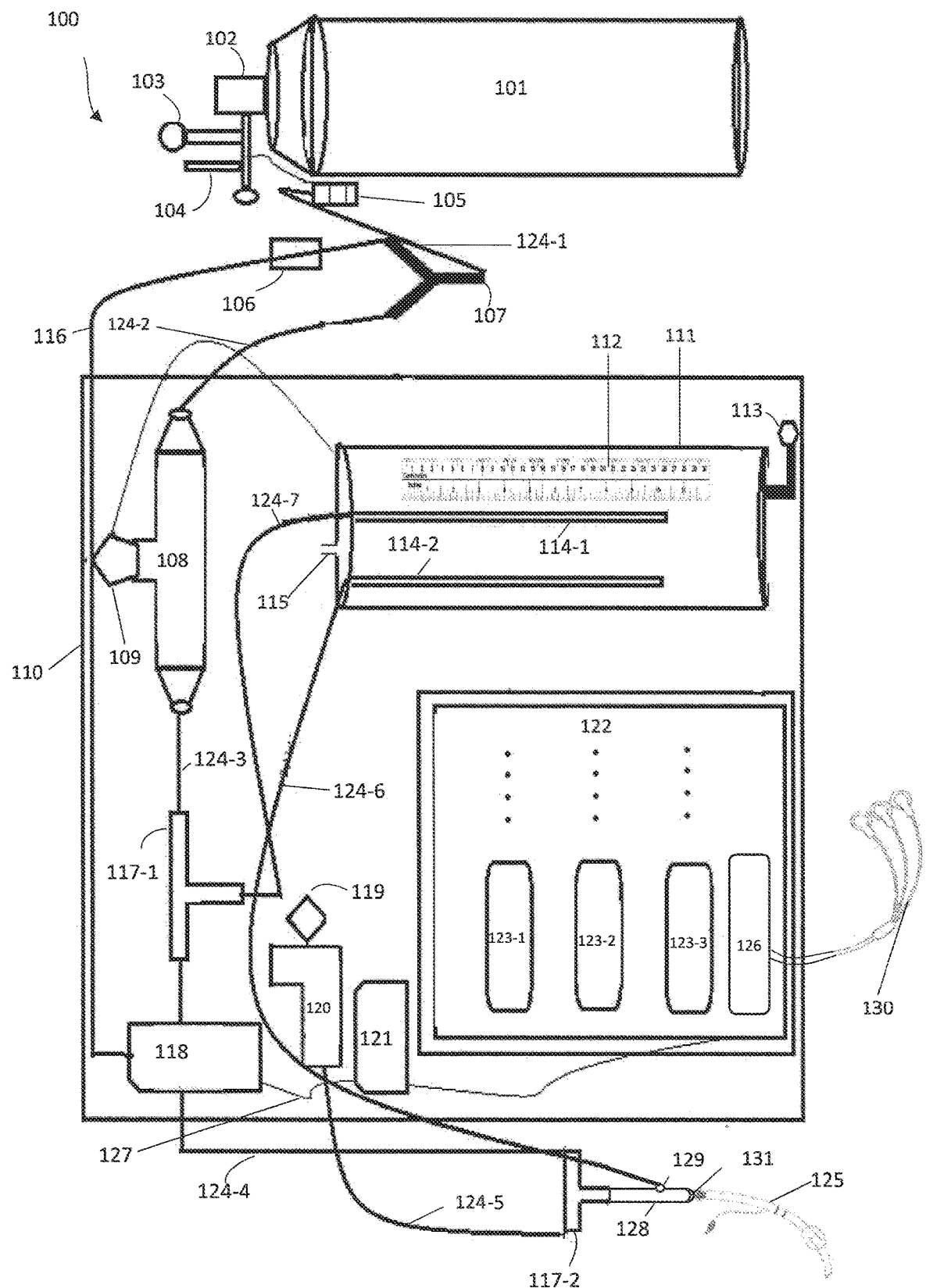
FIG. 1 illustrates, a ventilator system 100 in accordance with the present subject matter.

Referring now to FIG. 1, a ventilator system 100 is illustrated in accordance with the present subject matter. In one embodiment, the ventilator system 100 may be a portable system wherein the ventilator system 100 may be configured to ventilate a patient in the hospital or ambulance during transportation. The ventilator system 100 may comprise a large oxygen delivery cylinder 101 in the hospital or at least two small cylinders (not shown in figure) in series in the ambulance, an air delivery unit 118, a water manometer 111, a plurality of connecting tubes 124, a digital display unit 122, and an end respiratory pressure adjustment unit comprising a solenoid valve 120 and flow control knob 119. The solenoid valve 120 may comprise a piston. Positive end-expiratory pressure (PEEP) is the pressure in the lungs (alveolar pressure) that exists at the end of expiration. Pressure that is applied or increased during an inspiration is termed pressure support. Peak inspiratory pressure (PIP) is the highest level of pressure applied to the lungs during inspiration. Continuous positive airway pressure (CPAP) is the pressure applied without pause generally utilizing flow to generate the pressure. Further, inspiratory positive airway pressure forces air into the lungs, thus less work is required from the respiratory muscles. The ventilator system 100 is capable to deliver CPAP and IPAP with end respiratory pressure, required PEEP and number of required breaths. Further, the ventilator system 100 may also constantly provide reading of percentage of oxygen in the system.

In one embodiment, the oxygen delivery cylinder 101, may be a large cylinder 101 or two small cylinders. In one embodiment, the oxygen delivery cylinder 101 may be configured to supply low pressure oxygen via a humidifier 105 associated with the oxygen delivery cylinder 101. The oxygen delivery cylinder 101 may further comprise a pressure regulator valve 102, a safety gauge 103, and a flow meter 104. The oxygen may be supplied to the ventilator system 100 from a connecting tube 124-1 which connects the humidifier 105 associated with the oxygen delivery cylinder 101 and a Y connector 107. The air delivery unit 118 may be configured to deliver air in the ventilator system 100 via a tube 116, which may be a rubber tube, connecting the air delivery unit 118 and the Y connector 107 The amount of air delivery is easily adjustable. The Y connector 107 may be a hollow tube with shape Y, thus comprising three vents at each end of the shape Y. In one embodiment, the Y connector 107 may be configured to mix air and oxygen, to form a gas wherein, the air and oxygen is received from the air delivery unit 118 and the oxygen delivery unit 101 respectively at two vents of the Y connector 107. The third vent of the Y connector 107 may be configured to pass said gas towards an outlet 131 of the ventilator system 100. The ventilator system 100 may comprise a board 110 which may comprise some components such as the water manometer 111, a plurality of connecting tubes 124, the digital display unit 122, the solenoid valve 120, and a plurality of connecting elements. In one embodiment, the air delivery unit 118 may be positioned behind the board 110. The gas from the Y connector 107 may be passed through a connecting tube 124-2 to a T connector 108. In one embodiment, an oxygen sensor 109 may be positioned on the T connector 108 to measure the percentage of oxygen in the gas passed from the Y connector 107 in the ventilator system 100. In other words, the oxygen sensor 109 may be positioned at a connecting tube 124-2. In one embodiment, the oxygen sensor 109 may be a medical oxygen sensor. The T connector 108 comprise two reduced ends, wherein one end may receive gas from the Y connector 107 and the other end may pass the gas further to a first T connector 117-1 via a connecting tube 124-3. The first T connector 117-1 may be configured to pass the gas received from the T connector 108 to the water manometer 111 from a vent of the first T connector 117-1 by a connecting tube 124-7 between the first T connector 117-1 and the water manometer 111. The first T connector 117-1 may also be configured to pass the gas towards the outlet 131 of the ventilator system 100 from another vent of the first T connector 117-1.

In one embodiment, the ventilator system 101 may comprise a single water manometer 111. The water manometer 111 may comprises at least two burate tubes 114-1, 114-2, a measuring scale 112, a channel 115 and a drain valve 113. The water manometer 11 may be configured to monitor a pressure of the gas in the ventilator system 100 and blow off the excess pressure of the gas through a channel 115. The first burate tube 114-1 comprises gas from the first T connector 117-1 and the second burate tube 114-2 comprises gas from a dead space 128. The measuring scale 112 may be fixed on the wall of the water manometer 111 configured to illustrate pressure of the gas in the burate tubes 114-1, 114-2. The pressure of the gas in the burate tubes 114-1, 114-2 is adjusted and set by sliding the burate tubes 114-1, 114-2, in correspondence with the height of said burate tubes 114-1, 114-2, or adjusting the water level in water manometer 111 or a combination thereof. The water level may be adjusted by adding water from the top of the water manometer 111 or by removing the water in the water manometer 111 from the drain valve 113 in the bottom of the water manometer 111, thereby enabling a first check of the pressure of the gas in the ventilator system 100 which is delivered to a breathing device 125. In a preferred embodiment, the maximum pressure delivered to an infant is up to 30 cm of water. End respiratory pressure may be between 3 and 6 cm of water. The water manometer 111 may comprise of the measuring scale 112 of 30 cm scale for measuring the insertion of the burate tubes 114-1, 114-2 and also the water in the water manometer 111. In one embodiment, if the pressure in the water manometer 111 may be adjusted at 26 cm, wherein the reading on the measuring scale 112 may start from top to bottom, the burate tubes 114-1, 114-2 in the water manometer 111 may be inserted till 26 cm or as per required. In such a case, when the pressure in the water manometer 111 exceeds the stipulated pressure, the excess pressure may be blown off from the water manometer 111 in the form of bubbles and allow to escape the excess pressure from the channel 115 provided on the upper surface of the water manometer 111. In case the pressure in the water manometer 111 decreases than the stipulated pressure, then it may be visible on the digital display unit 122 comprising an LCD displaying the oxygen percentage in the gas being delivered to the breathing device 125. The required amount of oxygen may be supplied immediately. In another embodiment, if the pressure in the water manometer 111 is to be set at 26 cm, the water in the water manometer 111 may be filled up to 30 cm and the burate tubes 114-1, 114-2 may be inserted up to a level of 26 cm. Said pressure seen on the water manometer 111 may be the pressure delivered to the breathing device 125.

In one embodiment, said another vent of the first T connector 117-1 may be configured to pass the gas further to a first vent of a second T connector 117-2 via a connecting tube 124-4. A second vent of the second T connector 117-2 may be configured to pass an end respiratory pressure towards the end respiratory unit comprising the solenoid valve 120. The second vent of the second T connector 117-2 may be connected to the solenoid valve 120 by a connecting tube 124-5. The solenoid valve 120 may comprise a piston and a flow control knob 119. The third vent of the second T connector 117-2 may be configured to pass the gas to the breathing device 125 by connecting the breathing device 125 to outlet 131 of the ventilator system 100 through the dead space 128.

In one embodiment, the end respiratory pressure may be easily adjustable by the solenoid valve 120 through flow control knob 119. Said adjustment may be priorly done by fixing dummy lungs and setting the number of breath of the patient. The movement of the piston in the solenoid valve 120 may resemble the number of breaths of the patient. Therefore, an end respiratory pressure may be delivered to the breathing device 125. In other words, the solenoid valve 120 may be configured to adjust an end respiratory pressure, wherein the end respiratory pressure is obtained from the breathing device 125, wherein the breathing device 125 is connected to the outlet 131 of the ventilator system 100. The movement of the piston in the solenoid valve 120 may resemble the amount of breaths of the patient thereby delivering an end respiratory pressure to the patient. The solenoid valve 120 may be configured to regularly or constantly blow off the expiratory gas from the ventilator system 100 to the atmosphere.

In one embodiment, the pressure of the gas being instantly delivered to the breathing device 125 by the ventilation system 100 is measured by said water manometer 111 from a dead space 128, wherein the dead space 128 is near the outlet 131 of the ventilator system 100, thereby enabling a dual monitoring of the pressure of the gas being delivered to the breathing device 125. The dead space 128 may be between the third vent of the second T connector 117-2 and outlet 131, wherein the dead space 128 comprises a mixed gas of inspiration and expiration from the breathing device 125. The dead space 128 may comprise an aperture 129 such that a connecting tube 124-6 is configured to pass the gas from the aperture 129 in the dead space 128 to the second burate 114-2 in the water manometer 111, thereby enabling a second check of the pressure of gas being instantly delivered to the breathing device 125 by the ventilator system 100.

In one embodiment, the pressure adjusted in the water manometer 111 may be same delivered to the breathing device 125. In one embodiment, the breathing device 125 may be invasive or non-invasive device such as, but not limited to a nasal prong, an endotracheal tube, a laryngeal mask, face mask and such like for delivering the gas to the lungs of the patient.

In one embodiment, the digital display unit 122 comprises a plurality of LCDs 123-1, 123-2, 123-3 configured to display the plurality of measurements. The percentage of oxygen percentage in the gas sensed by the oxygen sensor 109 may be displayed on LCD 123-1. A ratio of number of breaths in and number of breaths out set by an operator of the ventilator system 100 may be displayed on LCD 123-2. In one embodiment, LCD 123-2 may display the number of breaths given to the patient by the command to the piston to open and close the exit of the gas. This gives the time of breath in and breath out. It facilitates variability of time to manage the oxygen and carbon dioxide in the patient's blood. For example, if carbon dioxide in the patient's blood goes up, the breath out time is increased and breath in time is decreased. A concentration of pressure of the air delivered from the air delivery unit 118 may be displayed on LCD 123-3. In one embodiment, the air delivery unit 118 may be connected electrically to LCD 123-3 via an AC to DC rectifier and wire 127. In one embodiment, the digital display unit 122 may comprise an ECG monitor and a breath monitor 126 configured to measure a heart activity via at least three electrodes 130. The digital display unit 122 may comprise few switches in order to operate the ventilator system 100 manually. In one embodiment, the ventilator system 100 may be fully or partially automated.

In one embodiment, a plurality of alarms may be set in the ventilation system 100. One alarm may be set at the exit of the oxygen delivery cylinder 101 to alert incase the oxygen pressure lowers indicating replacement. Second alarm may be a pressure sensor fixed after the level of water manometer 111. Third alarm may be fixed above the LCD 123-1 to alert if the oxygen percentage drops below 40%.

Therefore, the ventilator system 100 may compulsorily deliver stipulated pressure. The stipulated pressure cannot change unless done so by the manual operator of the ventilator system 100. The ventilator system 100 may be electric and pressure driven and not volume/gas driven.

In one embodiment, the dead space 128 between the breathing device 125 and the second T connector 117-2 may be less, ranging from 6 cm to 15 cm. Therefore, increase of $CO_2$ in the dead space 128 doesn't take place. Hence, both the lungs of the patient may receive required pressure through the breathing device 125 and with each breath of the patient the lungs may get inflated.

In one embodiment, the mixing of air with the oxygen may be performed as per requirement. The ventilator 100 may enable gas delivery through breathing device 125, wherein the breathing device 125 may be, but not limited to tracheal tube, mask, nasal prong and such like. In case of power failure, the ventilator system 100 may work on portable battery, battery of the ambulance or like sources. The ventilator system 100 may prevent against pneumothorax. The ventilator system 100 uses components which are easily available and are economic. The ventilator system 100 is therefore very cost efficient, easy to operate, digital, portable, and able to work during power failure.

In one embodiment, a second check for the pressure of the gas is enabled by projecting a connecting tube 124-6 through a dead space 128 and inserting a second burate 114-2 associated with said connecting tube 124-6 in the water manometer 111. This facilitates in knowing the exact pressure of gas being delivered to the patient via breathing device 125. Utilizing a 'single water manometer' for measuring gas pressure twice or multiple times by providing a second check to sense the pressure of the gas while it passes through the dead space 128 by using same water manometer 111. The advantage of this may be in identifying the exact airflow rate (in terms of pressure) at which the gas is delivered to the patient and further adjusting the rate in case need arises.

Figure 2:
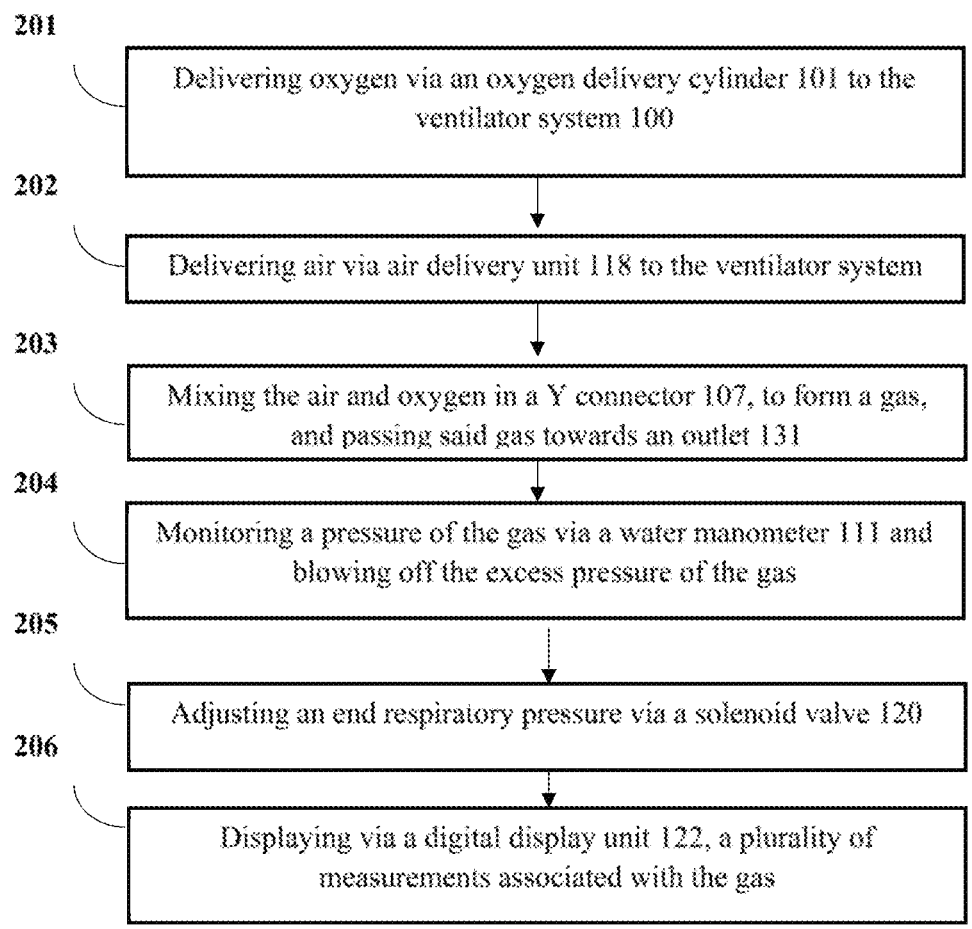
FIG. 2 illustrates, a method 200 of operating the ventilator system 100 in accordance with the present subject matter.

Referring now to FIG. 2, illustrates a method 200 of operating the ventilator system 100.

At step 201, the oxygen delivery cylinder 101 may deliver oxygen to the ventilator system 100.

At step 202, the air delivery unit 118 may deliver air to the ventilator system 100.

At step 203, the air and oxygen may be mixed in a Y connector 107, to form a gas, and said gas is passed towards an outlet 131 of the ventilator system 100. The air and oxygen is received from the air delivery unit 118 and the oxygen delivery unit 101 respectively.

At step 204, a pressure of the gas in the ventilator system 100 may be monitored via a water manometer 111 and blowing off the excess pressure of the gas through a channel 115. The water manometer 111 may be configured to monitor the pressure of the entire system 100 as well as the pressure of the gas being instantly delivered to the breathing device 125 by the ventilation system 100 is measured by said water manometer 111 from a dead space 128. The dead space 128 is near the outlet 131 of the ventilator system 100, thereby enabling a dual monitoring of the pressure of the gas being delivered to the breathing device 125.

At step 205, an end respiratory pressure may be adjusted via a solenoid valve 120, wherein the end respiratory pressure is obtained from a breathing device 125. The breathing device 125 is connected to the outlet 131 of the ventilator system 100.

At step 206, a plurality of measurements associated with the gas in the ventilator system 100 may be displayed via a digital display unit 122.

The ventilator system 100 may be an open system and not the one embedded in a box or hidden behind any screen or may be a closed system placed inside a housing or may be a semi-closed system. This may enable to detect any fault in the system easily wherein faults may comprise leakages in any tubes, or false working of the components in the ventilator system 100. In one embodiment, the system 100 may be used in hospitals, where the ventilator system 100 may be located in a fixed position. In another embodiment, the ventilator system 100 may be efficiently used in the ambulance also, hence in this scenario the ventilator system 100 may be portable. The ventilator system 100 may be handled by semi-skilled operators, as the system is not complex and easily adjustable. The ventilator system 100 is very cost effective as the components designed and used in the system are not expensive. The ventilator system 100 does not contain valves which could get stuck or lead to malfunctioning of the system 100. Thus, absence of valves in the tubings of the entire system enables the ventilator system 100 to be leakage proof. The pressure management in the ventilator system 100 may be performed by blowing off the excess pressure in the system 100 to the atmosphere. The ventilator system 100 does not contain any concealed tunnel of gas in the system which may lead to gas leakage and blockage, further leading to loss of pressure or excess pressure delivered to the lungs causing pneumothorax. In one embodiment, the connecting tubes 124 used in the ventilator system 100 may be, but not limited to, latex tubes which provide proper interconnectivity. The latex tubes are easily adjustable on diameters, have good grip and are leak proof. In a preferred embodiment, the ventilator system 100 comprises a single water manometer 111. This provides required accuracy and also reduces the cost of the ventilator system 100. In one embodiment, the ventilator system 100 may be configured to work on main supply of electricity in the hospitals, or through battery supply available from the ambulance or even in extreme power supply failure conditions wherein the ventilator system 100 may efficiently work on continuous positive airway pressure (CPAP) from the environmental air. Hence, the ventilator system 100 may work efficiently and safely with or without power supply. The ventilator system 100 may work during power failure as the pressure in the system 100 is maintained by blowing off excess pressure in the system with the help of water manometer 111.

In one embodiment, oxygen adjustment may be easily performed and constantly monitored. Further, excess pressure is blown off from the system, hence there is no chance wherein excess pressure may be delivered to the lungs. Therefore, the ventilator system 100 is very safely and efficiently operable with respect to pressure management in the system and in cases of complete electric power failure. The ventilator system 100 may be operated on wall oxygen also.

Although implementations of a ventilator system 100 and method 200 of operating the same have been described in language specific to structural features and/or methods, it is to be understood that the appended claims are not necessarily limited to the specific features or methods described. Rather, the specific features are disclosed as examples of a ventilator system 100 and method 200 of operating the same.

The invention claimed is:

1. A ventilator system, comprising:
an oxygen delivery cylinder;

an air delivery unit;
a plurality of connecting tubes;
a Y connector configured to mix air and oxygen, to form a gas and pass said gas towards an outlet of the ventilator system, wherein, the air and oxygen is received from the air delivery unit and the oxygen delivery unit respectively;
a water manometer configured to monitor a pressure of the gas in the ventilator system and blow off the excess pressure of the gas through a channel;
a solenoid valve configured to adjust an end respiratory pressure, wherein the end respiratory pressure is obtained from a breathing device, wherein the breathing device is connected to the outlet of the ventilator system; and
a digital display unit to display a plurality of measurements associated with the gas in the ventilator system;
wherein the pressure of the gas being instantly delivered to the breathing device by the ventilation system is measured by said water manometer from a dead space, wherein the dead space is near the outlet of the ventilator system, wherein the ventilator system comprises second T connector comprising three vents, wherein a first vent is configured to receive gas from the first T connector, a second vent is configured to pass the end respiratory pressure towards the solenoid valve, and a third vent configured to pass the gas to the breathing device by connecting the breathing device to outlet of the ventilator system through the dead space, thereby enabling a dual monitoring of the pressure of the gas being delivered to the breathing device.

2. The ventilator system as claimed in claim 1, wherein the oxygen delivery cylinder is configured to supply low pressure oxygen via a humidifier associated with the oxygen delivery cylinder.

3. The ventilator system as claimed in claim 1, wherein ventilator system comprises an oxygen sensor configured to measure the percentage of oxygen in the gas passed from the Y connector, wherein the oxygen sensor is positioned at a connecting tube.

4. The ventilator system as claimed in claim 1, wherein the ventilator system comprises a first T connector configured to pass the gas received from the Y connector to the water manometer through a vent of the first T connector and wherein another vent of the first T connector is used to pass the gas towards the outlet of the ventilator system.

5. The ventilator system as claimed in claim 1, wherein the water manometer comprises at least two burate tubes, a measuring scale, a channel and a drain valve, wherein the first burate tube comprises gas from the first T connector and the second burate tube comprises gas from the dead space, the measuring scale is fixed on the wall of the water manometer configured to illustrate pressure of the gas in the burate tubes, wherein the pressure of the gas in the burate tubes is adjusted and set by sliding the burate tubes in correspondence with the height of said burate tubes or adjusting the water level in water manometer or a combination thereof, wherein said water level is adjusted by adding water from the top of the water manometer or by removing the water in the water manometer from the drain valve in the bottom of the water manometer, thereby enabling a first check of the pressure of the gas in the ventilator system which is delivered to the breathing device.

6. The ventilator system as claimed in claim 1, wherein the dead space is between the third vent of the second T connector and outlet, wherein the dead space comprises a mixed gas of inspiration and expiration from the breathing device, wherein the dead space comprises an aperture such that a connecting tube is configured to pass the gas from the aperture in the dead space to the second burate in the water manometer, thereby enabling a second check of the pressure of gas being instantly delivered to the breathing device by the ventilator system.

7. The ventilator system as claimed in claim 1, wherein the digital display unit comprises a plurality of LCDs configured to display the plurality of measurements such as oxygen percentage in the gas sensed by the oxygen sensor, ratio of number of breaths in and number of breaths out set by an operator of the ventilator system, and concentration of pressure of the air delivered from the air delivery unit respectively and wherein the digital display unit comprises an ECG monitor and a breath monitor configured measure a heart activity via at least three electrodes.

8. The ventilator system as claimed in claim 1, wherein the plurality of connecting tubes are latex tubes configured to pass the gas in the ventilator system, wherein a connecting tube connects the humidifier to a vent of the Y connector in order to supply oxygen from the oxygen delivery cylinder, a connecting tube connects another vent of the Y connector and a vent of a T connector which comprises the oxygen sensor, a connecting tube connects another vent of the T connector to a vent of the first T connector, a connecting tube connects another vent of the first T connector to a first vent of the second T connector, a connecting tube connects a second vent of the second T connector to the solenoid valve, a connecting tube connects the aperture in the dead space to the second burate tube in the water manometer and a connecting tube connects yet another vent of the first T connector to the first burate tube in the water manometer, and wherein a tube is a rubber tube connecting the air delivery pump to yet another vent of the Y connector.

9. The ventilator system as claimed in claim 1, wherein the ventilator system is an open system or an enclosed system or a semi closed system, comprising a single water manometer, wherein the ventilator system is free of choking valves and spring based dial, thereby reducing the complexity, cost and maintenance of the ventilator system and wherein the ventilator system is configured to deliver a continuous positive airway pressure (CPAP) during power failure.

10. A method of operating the ventilator system comprising:
delivering oxygen via an oxygen delivery cylinder to the ventilator system;
delivering air via air delivery unit to the ventilator system;
mixing the air and oxygen in a Y connector, to form a gas, and passing said gas towards an outlet of the ventilator system, wherein, the air and oxygen is received from the air delivery unit and the oxygen delivery unit respectively;
monitoring a pressure of the gas in the ventilator system via a water manometer and blowing off the excess pressure of the gas through a channel;
adjusting an end respiratory pressure via a solenoid valve, wherein the end respiratory pressure is obtained from a breathing device, wherein the breathing device is connected to the outlet of the ventilator system;
displaying via a digital display unit, a plurality of measurements associated with the gas in the ventilator system;
wherein, the pressure of the gas being instantly delivered to the breathing device by the ventilation system is measured by said water manometer from a dead space, wherein the dead space is near the outlet of the ventilator system, wherein the dead space is between the third vent of the second T connector and outlet, wherein the dead space comprises a mixed gas of inspiration and expiration from the breathing device, wherein the dead space comprises an aperture such that a connecting tube is configured to pass the gas from the aperture in the dead space to the second burate in the water manometer, thereby enabling a second check of the pressure of gas being instantly delivered to the breathing device by the ventilator system, thereby enabling a dual monitoring of the pressure of the gas being delivered to the breathing device.

11. The method as claimed in claim 10 wherein, the water manometer comprises at least two burate tubes, a measuring scale, a channel and a drain valve, wherein the first burate tube comprises gas from the first T connector and the second burate tube comprises gas from the dead space, the measuring scale is fixed on the wall of the water manometer configured to illustrate pressure of the gas in the burate tubes, wherein the pressure of the gas in the burate tubes is adjusted and set by sliding the burate tubes, in correspondence with the height of said burate tubes, or adjusting the water level in water manometer or a combination thereof, wherein said water level is adjusted by adding water from the top of the water manometer or by removing the water in the water manometer from the drain valve in the bottom of the water manometer, thereby enabling a first check of the pressure of the gas in the ventilator system which is delivered to the breathing device.

* * * * *